United States Patent [19]
Fouin et al.

[11] Patent Number: 5,649,932
[45] Date of Patent: Jul. 22, 1997

[54] MYRINGOTOMY TUBE

[75] Inventors: Michel H. Fouin, Rouen, France; Christophe J. P. Sevrain, Ridgefield, Wash.

[73] Assignee: Advanced Microbotics Corporation, Portland, Oreg.

[21] Appl. No.: 558,541

[22] Filed: Nov. 16, 1995

[51] Int. Cl.$^6$ .............................. A61F 11/00; A61M 5/00
[52] U.S. Cl. ............................... 606/109; 604/256
[58] Field of Search ........................... 604/285, 280, 604/264, 256; 606/108, 109; 128/664

[56] References Cited

U.S. PATENT DOCUMENTS

| 3,645,268 | 2/1972 | Capote | 604/347 |
|---|---|---|---|
| 4,168,697 | 9/1979 | Cantekin | 128/350 |
| 4,174,716 | 11/1979 | Treace | 128/350 |
| 5,207,685 | 5/1993 | Cinberg et al. | 606/109 |
| 5,389,088 | 2/1995 | Hageman | 604/264 |
| 5,496,329 | 3/1996 | Reisinger | 606/109 |

OTHER PUBLICATIONS

French Patent Specification Document, "Drain Trans–Tympanique" (1988).

Primary Examiner—Robert A. Clarke
Assistant Examiner—David J. Cho
Attorney, Agent, or Firm—Klarquist Sparkman Campbell Leigh & Whinston, LLP

[57] ABSTRACT

A myringotomy tube is disclosed for transtympanic placement in an ear to ventilate the middle ear and relieve infection. The tube includes body with a bore that is angled to provide a view of portions of the middle ear that are not immediately in line with a longitudinal axis of the body. An extension member is attached to the body, and may be grasped by forceps to rotate the tube, and direct the line of view through the bore to different portions of the ear. Rotation of the body and its angled bore permits a panoramic view of the inner ear. The extension may also be grasped by forceps to extract the tube from the ear. Longer extensions, that protrude out of the external opening of the auditory canal, may be used for temporary placement and manual digital removal without requiring forceps.

10 Claims, 2 Drawing Sheets

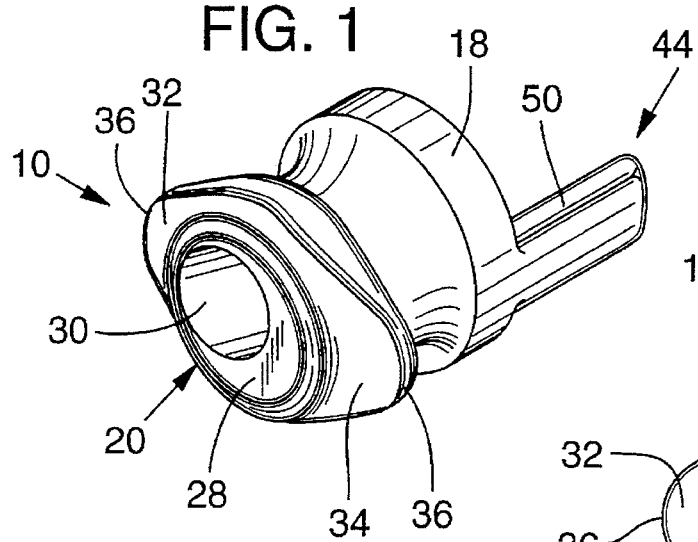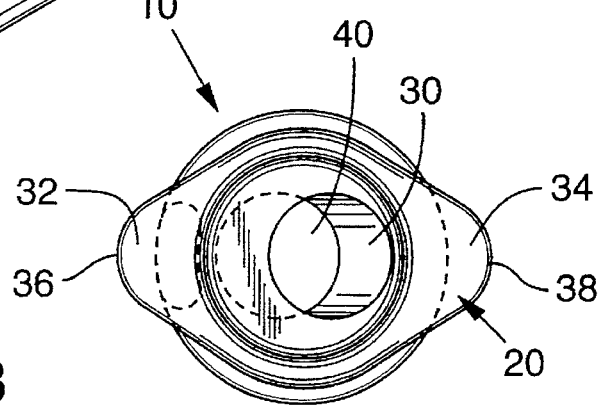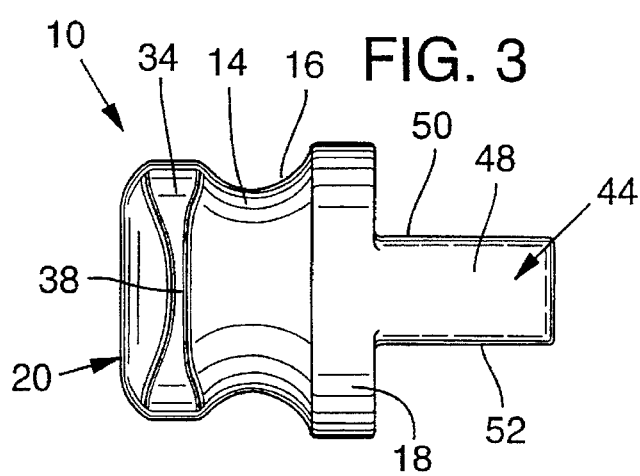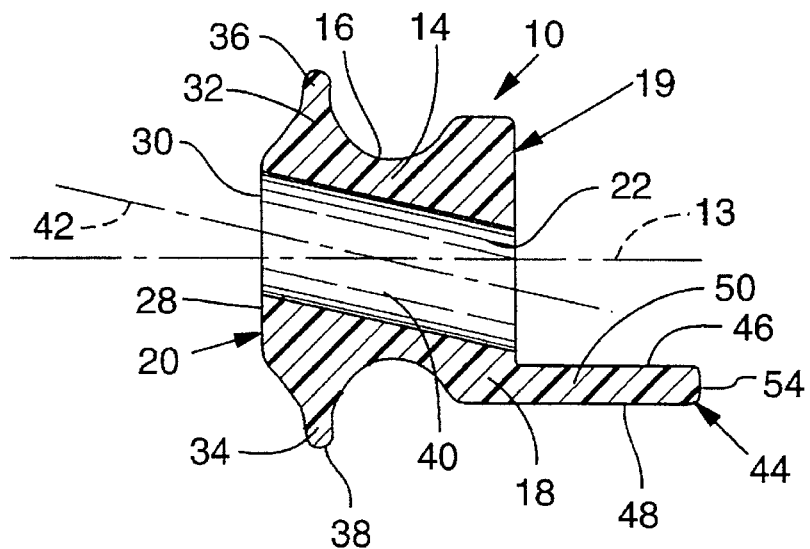

MYRINGOTOMY TUBE

FIELD OF THE INVENTION

This invention concerns transtympanic tubes for ventilation of the middle ear in patients with otitis media.

GENERAL DISCUSSION OF THE BACKGROUND

Recurrent otitis media is a painful condition, and is particularly prevalent in children. Some studies have suggested that otitis media occurs in 25% of children, and is frequently caused by *Streptococcus pneumoniae*.

Treatment of children with recurrent otitis media includes initial medical management with administration of antibiotics. Those patients who do not respond to antibiotic treatment, or who continue to relapse in spite of adequate antibiotic therapy, are treated with a surgical procedure known as a myringotomy. An incision is made in the tympanic membrane that separates the inner ear from the external ear, so that fluid can be aspirated from the inner ear. A myringotomy or tympanostomy tube may then be inserted at the site of the incision to maintain patency of the opening and allow ventilation of the middle ear. This procedure is commonly performed in children, and a variety of transtympanic tubes have been devised for this purpose.

Previous transtympanic tubes have been made of materials such as silicone rubber, and typically have a central necked-down portion that connects inner and outer flanges which help prevent displacement of the tube. Retention of this device through the myringotomy opening is desired because the tube preferably stays in place for a period of weeks to months. The tube also provides the advantage of permitting limited inspection of the middle ear through the bore of the tube using a conventional otoscope, or even fiberoptic equipment.

Prior myringotomy tubes suffer from the disadvantage of being difficult to remove once they have assumed their transtympanic position with the flanges holding them in place. Similarly, only a very limited area of the inner ear, directly in front of the tube, can be viewed through the open bore.

It is accordingly an object of the present invention to provide a myringotomy tube that is easier to remove than previous tubes.

Yet another object of the invention is to provide such a tube which provides a more panoramic view of the middle ear than afforded by prior art tubes.

SUMMARY OF THE INVENTION

The foregoing objects are achieved by a myringotomy tube having a body with a longitudinal axis of symmetry. The body has a tapered neck with an annular exterior channel around the neck that separates an outer collar of the body from an inner anchoring member. The collar has an outer disk-shaped face with a diameter greater than the neck, and the inner anchoring member has a largest diameter greater than both the neck and the outer face. A bore extends through the body along a longitudinal bore axis that intersects the longitudinal axis of the body at an angle of 5°–45°, preferably 10°–30°. A rigid extension member is attached to the outer face, and extends outwardly from the tube to allow for easier grasping and manipulation of the tube.

The angled bore allows an observer to view areas of the inner ear that are not immediately in front of the tube. This is an important feature, because the tube is typically placed through a myringotomy incision toward an edge of the tympanic membrane. Hence the angled bore provides a more panoramic view of the greater portion of the middle ear that is not immediately in front of the tube. The extension member greatly enhances the examiner's ability to view selected portions of the middle ear, because the extension member can be grasped with microsurgical tools to rotate the tube and view different selected areas of the middle ear. The extension member can also be grasped with forceps to extract the myringotomy tube from the tympanic membrane, and remove the tube from the ear.

BRIEF DESCRIPTION OF THE DRAWINGS

FIG. 1 is an enlarged, perspective view of the myringotomy tube of the present invention.

FIG. 2 is an end view of the myringotomy tube of FIG. 1, viewing the inner end, with portions being shown in phantom to illustrate the structural relationship.

FIG. 3 is a side view of the myringotomy tube of FIG. 1.

FIG. 4 is a cross-sectional view of the myringotomy tube of FIG. 1, the tube having been rotated ninety degrees around its longitudinal axis form the position shown in FIG. 1.

DETAILED DESCRIPTION OF PREFERRED EMBODIMENT

Figure 5:
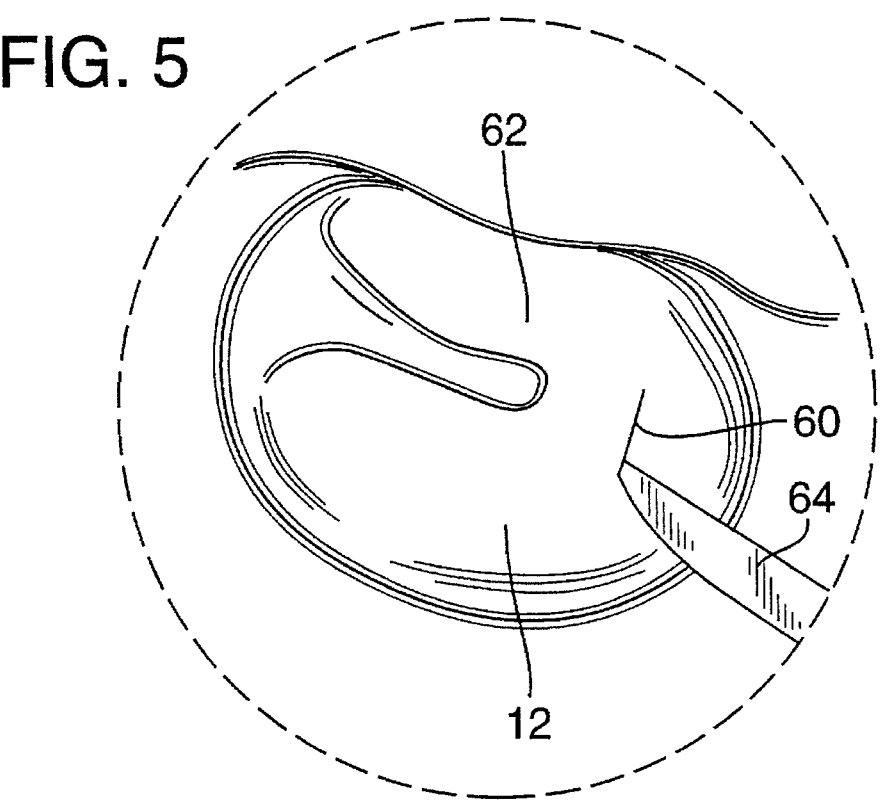
FIG. 5 is an enlarged view of the tympanic membrane of a human ear, as viewed externally, with the myringotomy incision being made through the tympanic membrane.
Figure 6:
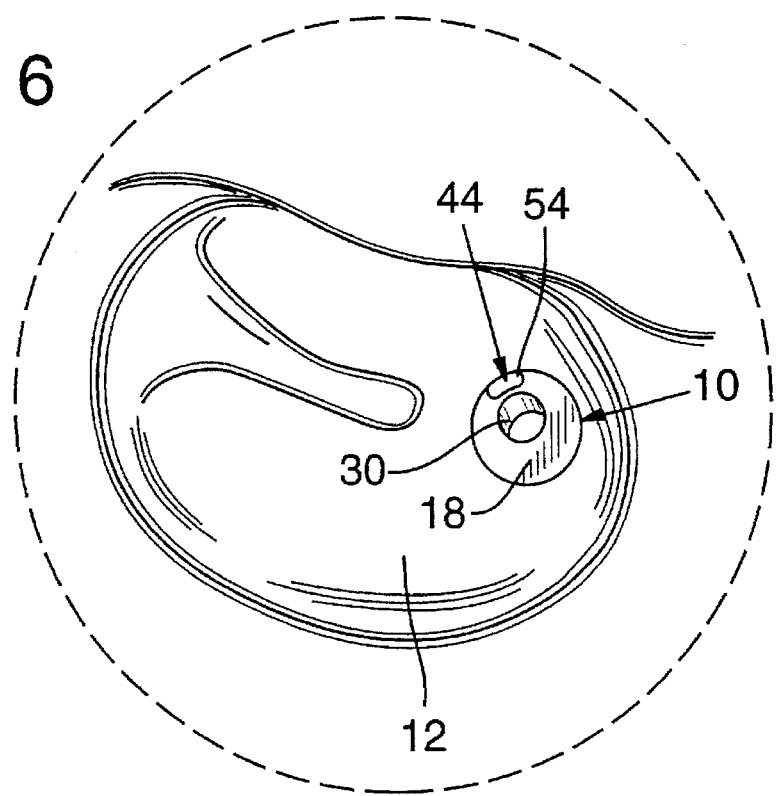
FIG. 6 is a view of the myringotomy tube after it has been introduced through the incision and the tympanic membrane is seated around the neck of the tube.

A myringotomy tube 10 is shown in the drawings for placement across a tympanic membrane 12 (FIGS. 5–6) of a human ear. The tube includes a body (the tube exclusive of an extension member) wherein the body has a longitudinal axis of symmetry 13 (FIG. 4). The body has a tapered neck 14 with an exterior channel 16 that separates an outer collar 18 of the tube from an inner anchoring member 20. Collar 18 is substantially cylindrical in cross section, and has a flat face 19 that will be referred to as the outer face of the tube (FIG. 4).

As best seen in FIG. 4, channel 16 has a generally semicircular cross-section. The preferred radius of of the semicircular channel is approximately 0.5–1 mm to provide a groove in which the tympanic membrane car seat.

The outer face 19 of collar 18 is a substantially flat disk circumscribing an outer bore opening 22. Outer face 19 has a diameter greater than a least diameter of neck 14 (at the narrowest portion of the tapering neck). The diameter of face 19 is the greatest diameter of collar 18, and is about 2 mm in the disclosed embodiment. In other embodiments, the diameter of face 19 may be 2–6 mm.

Inner anchoring member 20 is elongated transverse to longitudinal axis 13 of the tube. Member 20 comprises a central disk-shaped planar portion 28 (FIG. 1) that circumscribes an inner bore opening 30. First and second wings 32, 34 extend away from planar portion 28 in opposite directions, generally perpendicular to axis 13. Each of wings 32, 34 tapers in width and thickness as the wings extend away from the planar portion 28. The wings taper to a tip with an arcuate leading edge 36, 38. The greatest diameter of anchoring member 20 is between the leading edges 36, 38. In the disclosed embodiment, the greatest diameter of anchoring member is about 3 mm, but can vary widely, for example from 2–10 mm, preferably 2–4 mm.

A bore 40 extends through the body and interconnects outer bore opening 22 and inner bore opening 30. In the disclosed embodiment, the length of the body is about 2 mm along axis 13, but bore 40 is slightly longer (by about 1 mm) because of an inclined path it follows through the body. As with the other dimensions of the tube, the length of the body may vary, for example between 2 to 6 mm.

Bore 40 has the shape of an inclined cylinder with a longitudinal axis 42 that intersects longitudinal axis 13 at an angle (axis 42 is not parallel to axis 13). The angle of intersection is shown as about 10 degrees in the disclosed embodiment. The angle may vary, however, from 5–45 degrees, preferably 10–30 degrees, most preferably about 8–10 degrees.

A rigid elongated extension member 44 is attached to and extends outwardly at least 3 mm (for example 3–10 mm) from outer face 19, with an inner face 46 of member 44 (FIG. 4) in a plane tangential to a peripheral edge of outer bore opening 22. Member 44 also extends parallel to the longitudinal axis 13. In one disclosed embodiment, member 44 has flat, rectangular, parallel front and rear faces 46, 48 (FIG. 4), and rectangular parallel side faces 50, 52 (FIGS. 1, 3 and 4). All the faces meet along a flat tip face 54 that is perpendicular to faces 46, 48, 50, 52. Faces 46, 48 are preferably perpendicular to faces 50, 52. These flat faces provide ideal surfaces for grasping the extension member with a forceps to manipulate the tube.

In use, a myringotomy incision 60 is made through tympanic membrane 62 in a known fashion with an appropriate scalpel or other microsurgical instrument 64. The tube is then grasped by member 44 with a convention surgical forceps (not shown), and inserted through the myringotomy incision in a known fashion, with the wings 36, 38 of the anchoring member acting as a "shoehorn" to help introduce the inner end of the tube through the incision 60.

Once the tube is in place, the middle ear may be viewed through the bore 40 with a conventional or fiberoptic otoscope. The tilt of the bore allows the examiner to view portions of the middle ear that are not immediately adjacent the tube along axis 13. The view may be further expanded to provide a more panoramic examination of the middle ear by rotating the tube around axis 13, thereby moving axis 42 through a conical path. Rotation of the tube is achieved by grasping extension member 44 with a forceps (not shown) to rotate the body around axis 13. The forceps preferably has opposing faces that appose and frictionally engage faces 46, 48 of the member. However faces 50, 52 may also be engaged to rotate the tube.

Dimensions of the myringotomy tube given in this specification are merely for illustration. Any dimensions may be used that provide a suitable tube for transtympanic placement in the species of subject being treated. The length of extension member 44 may also be varied depending on the purpose for which the extension member will be used. A 3 mm extension member that is entirely contained within the external auditory canal is suitable for being grasped by the tips of a surgical forceps. A 10–15 mm long extension member is more suitable for temporary placement of a tube in which the extension member extends out of the external auditory canal. This longer extension member may be manually grasped by the fingers, and the tube extracted from the ear by pulling the extension member outwardly.

The myringotomy tube of the present invention may be made of a variety of biocompatible materials. For example, the tube may be made of metal or plastic, particularly polyethylene, or any plastic approved by regulatory agencies for use in the human body (if human use is intended). Other less biocompatible materials may be coated with a biocompatible material to render it more suitable for surgical applications.

Having illustrated and described the principles of the invention with reference to one preferred embodiment, it should be apparent to those persons skilled in the art that such invention may be modified in arrangement and detail without departing from such principles. All such modifications are claimed that come within the true spirit and scope of the following claims.

What is claimed is:

1. A myringotomy tube having a body for transtympanic placement across the trympanic membrane in an ear, wherein the tube comprises:

a tapering neck having an annular exterior channel therearound that separates an outer face of the body from an inner anchoring member, wherein the neck has a substantially circular cross-section that allows the tube to rotate when the body is in the tympanic placement with the tympanic membrane seated in the channel;

an outer collar having a least a diameter greater than a least diameter of the neck;

the inner anchoring member having a diameter greater than the neck and the outer collar;

a bore extending through the tube along a longitudinal bore axis that intersects a longitudinal axis of the tube at an angle of 5–45 degrees; and a rigid extension member attached to the outer face and extending outwardly therefrom, wherein the extension member comprises a strip projecting away from the outer face, parallel to the longitudinal axis of the tube, with the strip projecting substantially tangential to the outer edge of the outer collar.

2. The myringotomy tube of claim 1 wherein the outer face is planar, and the inner anchoring member comprises a central planar face and first and second elongated wings tapering in width and thickness as the wings extend away from the central planar face, and away from the longitudinal axis of the tube.

3. The myringotomy tube of claim 1 wherein the bore is an inclined cylindrical bore that extends through the tube from an outer bore opening in the outer face at a base of the rectangular strip, to an inner bore opening on the central planar face closer to the first elongated wing than the second elongated wing.

4. The myringotomy tube of claim 1 wherein the strip projects away from the outer face a distance that is at least as great as a longitudinal length of the body.

5. A myringotomy tube for transtympanic placement across a tympanic membrane in an ear, wherein the tube comprises:

a body having a tapering neck, an inner anchoring member, and an outer collar, the body having a longitudinal axis of symmetry;

the neck having an exterior channel that separates the outer collar of the tube from the inner anchoring member, the neck having a generally circular cross-section around which an annular channel extends, to allow the tube to rotate when the body is in the tympanic membrane, with the tympanic membrane seated in the channel, and the channel has a substantially semi-circular shape;

the collar comprises an outer face that is a substantially flat disk circumscribing an outer bore opening, and the collar has a diameter greater than a least diameter of the neck;

the inner anchoring member is elongated transverse to a longitudinal axis of the tube, and comprises a central disk-shaped planar portion that circumscribes an inner bore opening, and first and second wings that extend away from the central planar portion and each other, the wings tapering in width and thickness as the wings extend away from the central planar portion, and forming tips with arcuate leading edges;

a bore extending through the tube from the outer bore opening to the inner bore opening, the bore having the shape of an inclined cylinder with a longitudinal axis that intersects the longitudinal axis of the body at an angle of 5°–45 degrees; and a rigid elongated extension member attached to and extending outwardly from the outer face, parallel to the longitudinal axis of the body, the extension member having flat, and parallel front and rear faces and flat, parallel side faces to facilitate grasping the extension member with a tool and manipulating the tube.

6. The myringotomy tube of claim 5 wherein the flat faces of the extension member are all rectangular.

7. The myringotomy tube of claim 5 wherein the extension member extends perpendicularly at least 3 mm outwardly from the outer face.

8. The myringotomy tube of claim 5 wherein the extension projects from a peripheral edge of the outer face, and is tangential to the outer bore opening.

9. The myringotomy tube of claim 8 wherein a peripheral edge of the inner bore opening substantially coincides with a peripheral edge of the disk-shaped planar portion of the inner face.

10. A myringotomy tube for transtympanic placement in an ear, wherein the tube comprises:

a body comprising a tapering neck, an inner anchoring member, and an outer collar, the body having a longitudinal axis of symmetry;

the neck having an exterior channel that separates the outer collar of the tube from the inner anchoring member, the neck having a generally semi-circular cross-section around which the channel extends, wherein the channel is also generally semi-circular in shape and has a radius of curvature of approximately 0.5 mm–1 mm;

the collar comprises an outer face that is a substantially flat disk circumscribing an outer bore opening, and the collar has a diameter greater than a least diameter of the neck;

the inner anchoring member is elongated transverse to a longitudinal axis of the tube, and comprises a central disk-shaped planar portion that circumscribes an inner bore opening, and first and second wings that extend away from the central planar portion and each other, the wings tapering in width and thickness as the wings extend away from the central planar portion, and forming tips with arcuate leading edges that have a radius of curvature of 0.5–1 mm;

a bore extending through the tube from the outer bore opening to the inner bore opening, the bore having the shape of an inclined cylinder with a longitudinal axis that intersects the longitudinal axis of the body at an angle of 10–30 degrees; and a rigid elongated extension member attached to and extending outwardly at least 3 mm from the outer face, substantially tangential to a peripheral edge of the outer bore opening and parallel to the longitudinal axis of the body, the extension member having flat, rectangular parallel front and rear faces and flat, rectangular parallel side faces to facilitate grasping the extension member with a tool and manipulating the tube.

* * * * *